United States Patent

Barnes et al.

Patent Number: 5,726,129
Date of Patent: Mar. 10, 1998

[54] PYRROLIDINE-2-THIONE DERIVATIVES AS HERBICIDES

[75] Inventors: Nigel John Barnes, Maidenhead; Richard Anthony Barber, Reading, both of United Kingdom

[73] Assignee: Zeneca Limited, London, England

[21] Appl. No.: 737,538

[22] PCT Filed: May 26, 1995

[86] PCT No.: PCT/GB95/01223

§ 371 Date: Nov. 12, 1996

§ 102(e) Date: Nov. 12, 1996

[87] PCT Pub. No.: WO95/33718

PCT Pub. Date: Dec. 14, 1995

[30] Foreign Application Priority Data

Jun. 2, 1994 [GB] United Kingdom ............ 9411008

[51] Int. Cl.⁶ .................. A01N 43/36; C07D 207/27
[52] U.S. Cl. .................................. 504/283; 548/544
[58] Field of Search ........................ 548/544; 504/283

[56] References Cited

U.S. PATENT DOCUMENTS

| 3,818,032 | 6/1974 | Moser et al. ............... 548/116 |
| 4,956,006 | 9/1990 | Woolard ..................... 504/283 |
| 5,108,482 | 4/1992 | Lang et al. .................. 504/104 |

FOREIGN PATENT DOCUMENTS

| 397602 | 11/1990 | European Pat. Off. |
| 1345159 | 1/1974 | United Kingdom . |
| 94/13652 | 6/1994 | WIPO . |

*Primary Examiner*—Fiona T. Powers
*Attorney, Agent, or Firm*—Joseph R. Snyder

[57] ABSTRACT

Pyrrolidine-2-thione derivatives of the formula (I)

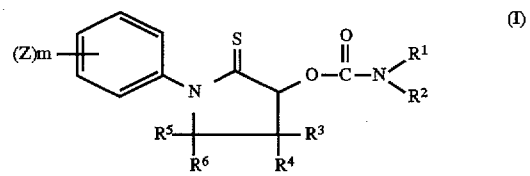

wherein the variables are as defined in the specification are active as herbicides.

9 Claims, No Drawings

PYRROLIDINE-2-THIONE DERIVATIVES AS HERBICIDES

This application is a 371 of PCT/GB95/01223 filed May 26 1995.

This invention relates to chemical compounds useful as herbicides, to processes for preparing them, and to herbicidal compositions and processes utilising them.

Herbicidal compounds based upon carbonyl substituted nitrogen containing heterocyclic rings are known for example from British Patent No. 1345159 and DE OS 2212558.

The applicants have found a group of compounds which have a particular substituent pattern and which are active as herbicides.

According to the present invention there is provided a compound of formula (I):

Wherein $R^1$ and $R^2$ are each independently hydrogen, optionally substituted lower hydrocarbyl, or optionally substituted heteroaryl, or $R^1$ and $R^2$ together with the nitrogen atom to which they are attached, form a heterocyclic ring; $R^3$, $R^4$, $R^5$ and $R^6$ are independently H or $C_{1-4}$ alkyl; Z represents halogen, optionally substituted lower hydrocarbyl, optionally substituted lower hydrocarbyloxy, optionally substituted lower hydrocarbylthio, hydrocarbylsulphinyl, or hydrocarbylsulphonyl, cyano, nitro, CHO, NHOH, $ONR^7R^{7''}$, $SF_5$, CO(optionally substituted lower hydrocarbyl), acylamino, $COOR^7$, $SO_2NR^8R^9$, $CONR^{10}R^{11}$, $OR^{12}$ or $NR^{13}R^{14}$ where $R^7$, $R^{7'}$, $R^{7''}$, $R^8$, $R^9$, $R^{10}$ and $R^{11}$ are independently H or lower hydrocarbyl; $R^{12}$ is hydrogen, $SO_2$ lower hydrocarbyl or $COR^{15}$; $R^{13}$ and $R^{14}$ are independently lower hydrocarbyl, lower hydrocarbyloxy or a group $R^{12}$; $R^{15}$ is $OR^{16}$, $NR^{17}R^{18}$, hydrogen or lower hydrocarbyl; $R^{16}$ is lower hydrocarbyl, $R^{17}$ and $R^{18}$ are independently hydrogen or lower hydrocarbyl provided that when there are two or more substituents Z, they may be the same or different; and m is 0 or an integer from 1 to 5.

The expression lower hydrocarbyl in the foregoing definitions, whether the expression is used on its own or as part of a larger radical such as for example lower hydrocarbyloxy, is intended to include hydrocarbyl radicals of, for example, up to ten carbon atoms. Subclasses of such hydrocarbyl radicals include radicals with up to four, or up to six carbon atoms. The expression hydrocarbyl is intended to include within its scope aliphatic, alicyclic, and aromatic hydrocarbyl groups and combinations thereof. It thus includes, for example, alkyl, alkenyl, and alkynyl radicals, cyclopropyl, cyclopropylmethyl, cyclobutyl, cyclopentyl, and cyclohexyl radicals, the adamantyl radical and the phenyl radical.

When the lower hydrocarbyl group is substituted, the substituents may include, for example, halogen (i.e. chlorine, bromine, fluorine or iodine), hydroxy, $SO_2NR^aR^b$ (where $R^a$ and $R^b$ are independently H or $C_{1-6}$ alkyl), cyano, nitro, amino, mono- and dialkylamino in which the alkyl groups have from 1 to 6 or more carbon atoms, acylamino, $C_{1-6}$ alkoxy, $C_{1-6}$ haloalkoxy, $C_{1-6}$ alkylthio, $C_{1-6}$ alkylsulphinyl, $C_{1-6}$ alkylsulphonyl, carboxy, carboxyamide in which the groups attached to the N atom may be hydrogen or optionally substituted lower hydrocarbyl; alkoxy carbonyl wherein the alkoxy group may have from 1 to 6 or more carbon atoms, and aryl such as phenyl.

The expression heteroaryl in the foregoing definitions is intended to include such radicals as pyridyl, pyrimidyl, triazinyl, thienyl, furyl, and thiazolyl. When the heteroaryl radical is substituted, the substituents may include those recited above for substituted lower hydrocarbyl.

Particular examples of values for $R^1$ and $R^2$ include hydrogen, methyl, ethyl, propyl, iso-propyl, n-butyl, iso-butyl, sec-butyl, t-butyl, n-pentyl and its isomers such as $C(CH_3)_2CH_2CH_3$, n-hexyl and its isomers, n-heptyl and its isomers, $C(CH_3)_2C\equiv CH$, $C(CH_3)CH=CH_2$, $C(CH_3)_2CN$, alpha-methyl benzyl, cyclohexyl, cyclopentyl, cyclobutyl, cyclopropyl, 1-methyl cyclohexyl, 1-methyl-cyclopentyl, 1-methyl-cyclobutyl, 1-methyl-cyclopropyl, 1-cyano-cyclohexyl, 1-cyano-cyclopentyl, 1-cyano-cyclobutyl, 1-cyano-cyclopropyl, 1-ethynyl-cyclohexyl, 1-ethynyl-cyclopentyl, 1-ethynyl-cyclobutyl, 1-ethynyl-cycloypropyl, phenyl, p-chlorophenyl and benzyl. When $R^1$ and $R^2$ together with the nitrogen atom to which they are attached, form a heterocyclic ring, the ring may be for example a pyrrolidino, piperidino, thiomorpholino or morpholino ring, each of which may be substituted, e.g. with one or more methyl groups.

Examples of particular values for Z include methyl, ethyl, n-propyl, iso-propyl, trifluoromethyl, difluoromethyl, pentafluoroethyl, trichloromethyl, ethoxyvinyl, fluorine, chlorine, bromine, iodine, methoxy, ethoxy, n-propoxy, iso-propoxy, trifluoromethoxy, tetrafluoroethoxy, cyano, nitro, amino, mono- or dialkylamino in which each alkyl group may have from 1 to 6 or more carbon atoms, hydroxylamino, acyl (e.g. acetyl or trifluoroacetyl), methylthio, methylsulphinyl, methylsulphonyl, trifluoromethylthio, trifluoromethylsulphinyl, trifluoromethylsulphonyl, sulphonamido, carboxy, alkoxycarbonyl in which the alkoxy group may have from 1 to 6 or more carbon atoms, carboxyamide in which the groups attached to the N atom may be hydrogen or optionally substituted lower hydrocarbyl; or acylamino (e.g. acetamido). When there is more than one substituent Z, the substituents may be the same or different.

Preferred values for Z are $CF_3$, $OCF_3$, $OCHF_2$, $CHF_2$, OMe, F, Cl, Br, I, $NH_2$, $NO_2$, CN, $C_{1-4}$alkyl, $C_{1-4}$alkoxy, $COC_{1-4}$alkyl, $NHCDC_{1-4}$alkyl, $SO_2C_{1-4}$alkyl, $OCF_2CHF_2$, $CF_2CF_3$, $OCF_2CHF_2$ and $SO_2NR^8R^9$.

Especially preferred values for Z are $CF_3$, $OCF_3$, $OCH_3$, F, Cl, Br and I.

m is preferably 1, 2 or 3.

The preferred substitution pattern for the Z groups is for a single Z group at the 3-position; or two Z groups at the 3,4- and 3,5- positions; or three Z groups at the 3, 4 and 5 positions, the Z group at the 4-position being halo, especially fluoro.

$R^1$ is preferably iso-propyl, sec-butyl, t-butyl, $C(CH_3)_2C\equiv CH$, $C(CH_3)_2CH=CH_2$, $C(CH_3)_2CH_2CH_3$ or a 3–6 membered cyloalkyl, optionally substituted by $CH_3$ or $C\equiv CH$ at the α position of the cycloalkyl ring.

$R^2$ is preferably hydrogen or $C_{1-4}$alkyl, especially hydrogen.

Preferably $R^3$, $R^4$, $R^5$ and $R^6$ are hydrogen.

The formula (I) given above is intended to include tautomeric forms of the structure drawn, as well as physically distinguishable modifications of the compounds which may arise, for example, from different ways in which the molecules are arranged in a crystal lattice, or from the inability of parts of the molecule to rotate freely in relation to other parts, or from geometrical isomerism, or from intra-molecular or inter-molecular hydrogen bonding, or otherwise.

Compounds of the invention exist in enantiomeric or diastereomeric forms. The invention includes all individual forms and mixtures thereof in all proportions.

Particular examples of compounds of the invention are listed in Table I.

TABLE I

| Compound No | Z(m) | $R^1$ | $R^2$ | $R^3$ | $R^4$ | $R^5$ | $R^6$ |
|---|---|---|---|---|---|---|---|
| 1 | 3-$CF_3$ | $C(Me)_3$ | H | H | H | H | H |

Compounds of formula {I} are suitably prepared by a variety of processes.

In particular compounds of formula (I) can be prepared by reacting a compound of formula (II) where $R^1$, $R^2$, $R^3$, $R^4$, $R^5$ and $R^6$ Z and m are as defined in relation to formula (I): with Lawessons Reagent (formula III) in a solvent such as toluene at 80° to 115° C. in the presence of a base. Suitable bases include weak bases such as triethylamine, pyridine or N-ethyl-N,N-diisopropyl amine.

Compounds of formula (II) can be prepared by reacting a compound of formula (IV) where $R^3$, $R^4$, $R^5$, $R^6$, Z and m are as defined in relation to formula (I): with a compound of formula (V) or, where $R^2$ is hydrogen, a compound of formula (VI) where $R^1$ is as defined in relation to formula (I) and $R^{19}$ is a leaving group in the presence of a base.

Suitable bases include weak bases such as triethylamine, pyridine or N-ethyl-N,N-diisopropyl amine.

Suitable leaving groups $R^{19}$ include halogen such as chloro.

The reaction is suitably effected in an organic solvent such as dichloromethane, trichloromethane, tetrahydrofuran or diethyl ether at temperatures of from 0° to 80° C., preferably at ambient temperature.

An alternative method of preparing compounds of formula from compounds of formula (IV) is by reacting the compound of formula (IV) with $ClC(O)OCH(Cl)CCl_3$ in the presence of a base to product a compound of formula (XIII) in which $R^3$, $R^4$, $R^5$, $R^6$, Z and m are as defined in relation to formula (I). The reaction is suitably carried out at from −10° to 10° C. in the presence of a solvent. Suitable bases are heteroaromatic nitrogen bases, such as pyridine. Suitable solvents are dichloromethane or chloroform. The compounds of formula (XIII) are then reacted with an amine of formula (VIII) $HNR^1R^2$ where $R^1$ and $R^2$ are as defined in relation to formula (I) to produce a compound of formula (I). The reaction is suitably carried out at from −10° to 30° C. in the presence of a base, and a solvent. Suitable bases are pyridine, and triethylamine. Suitable solvents are dichloromethane or chloroform. The compounds of formula (XIII) need not be isolated, but can be reacted in situ with the compound of formula (VIII).

Instead of $ClC(O)OCH(Cl)CCl_3$ the compounds of formula (IV) as defined above may be reacted with phosgene to produce a compound of formula (XIV) in which $R^3$, $R^4$, $R^5$, $R^6$ Z, and m are as defined in relation to formula (I). The compounds of formula (XIV) are then reacted with amine of formula (VIII) as hereinbefore defined to produce a compound of formula (I). The reaction is suitably carried out at from −20° to 50° C. in the presence of a base and a solvent.

Suitable bases are pyridine or triethylamine. Suitable solvents are chloroform, dichloro methane or tetrahydrofuran. The compound of formula (XIV) need not be isolated and can be reacted in situ with the compound of formula (VIII).

Alternatively compounds of formula (IV) may be produced by hydrolysis of a compound of formula (VII): where $R^3$, $R^4$, $R^5$, $R^6$, Z and m are as defined in relation to formula (I) and $R^{20}$ is $OCOR^{21}$. The reaction is conveniently carried out in the presence of an alcohol, such as methanol, and silica gel.

Suitably group $R^{21}$ is trifluoromethyl. The reaction is suitably effected in a solvent such as dichloromethane at temperatures of from 0° to 50° C., preferably ambient temperature.

Compounds of formula (IV) may be also be prepared by oxygenating a compound of formula (X), where $R^3$, $R^4$, $R^5$, $R^6$, Z and m are as defined in relationship to formula (I), with a strong base such as $LiN(SiMe_3)_2$ or $LiN(iPr)_2$, followed by reaction with a compound of formula (XVII).

The reaction is suitably effected in a solvent such as tetrahydrofuran at temperatures of from −100° to 30° C., preferably from −80° to 0° C. In compounds of formula (XVII) Ar is suitably a p-tolyl group and Ar' is suitably phenyl.

Where the substituents Z are of a nature and distribution to activate the phenyl ring to nucleophilic substitution it is possible to couple a compound of formula (XI); where Z and m are as defined and $R^{22}$ is a leaving group, with a compound of formula (XII); where $R^3$, $R^4$, $R^5$, and $R^6$, are as defined in relationship to formula (I), in the presence of a base.

Suitable leaving groups $R^{22}$ include halogen such as fluoro.

Suitable bases include strong bases such as potassium hydroxide or sodium hydroxide.

The reaction is suitably effected in an organic solvent such as dimethylsulphoxide or dimethylformamide at temperatures of from 0° to 90° C.

Examples of suitable compounds of formula (XI) include 3,4-difluoro-5-chloro-α,α,α-trifluorotoluene and 3,4,5-trifluoro-α,α,α-trifluorotoluene.

Compounds of formula (X) where $R^3$, $R^4$, $R^5$ and $R^6$ are hydrogen and Z and m are as defined in relationship to formula (I), may be prepared by heating and decarboxylating a compound of formula (XX) were $R^3$, $R^4$, $R^5$ and $R^6$ are hydrogen and Z and m are as defined in relationship to formula (I). Compounds of formula (XX) may be produced by reacting a compound of formula (XVIV) where Z and m are as defined in relationship to formula (I), with a compound of formula (XXI) prepared according to the method described in Organic Syntheses Vol 60 p66–68.

Compounds of formula (V), (VI), (VIII), (XI), (XII) and (XIV) are known compounds or may be prepared from known compounds by known methods.

Variations of the above procedures will be apparent to the skilled person in the art, as well as alternative processes for preparing the compounds of the invention.

The compounds of formula (I) above are active as herbicides, and the invention therefore provides in a further aspect a process for severely damaging or killing unwanted plants, which process comprises applying to the plants, or to the growth medium of the plants, a herbicidally effective amount of a compound of formula (I) as hereinbefore defined.

The compounds of formula (I) are active against a broad range of weed species including monocotyledonous and dicotyledonous species. They show some selectivity towards certain species; they may be used, for example, as selective herbicides in soya and maize crops. The compounds of formula (I) are applied directly to unwanted plants (post-emergence application) but they are preferably applied to the soil before the unwanted plants emerge (pre-emergence application).

The compounds of formula (I) may be used on their own to kill or severely damage plants, but are preferably used in the form of a composition comprising a compound of formula (I) in admixture with a carrier comprising a solid or liquid diluent.

Compositions containing compounds of formula (I) include both dilute compositions, which are ready for immediate use, and concentrated compositions, which require to be diluted before use, usually with water. Preferably the compositions contain from 0.01% to 90% by weight of the active ingredient. Dilute compositions ready for use preferably contain from 0.01 to 2% of active ingredient, while concentrated compositions may contain from 20 to 90% of active ingredient, although from 20 to 70% is usually preferred.

The solid compositions may be in the form of granules, or dusting powders wherein the active ingredient is mixed with a finely divided solid diluent, e.g. kaolin, bentonite, kieselguhr, dolomite, calcium carbonate, talc, powdered magnesia, Fuller's earth and gypsum. They may also be in the form of dispersible powders or grains, comprising a wetting agent to facilitate the dispersion of the powder or grains in liquid. Solid compositions in the form of a powder may be applied as foliar dusts.

Liquid compositions may comprise a solution or dispersion of an active ingredient in water optionally containing a surface-active agent, or may comprise a solution or dispersion of an active ingredient in a water-immiscible organic solvent which is dispersed as droplets in water.

Surface-active agents may be of the cationic, artionic, or non-ionic type or mixtures thereof. The cationic agents are, for example, quaternary ammonium compounds (e.g. cetyltrimethylammonium bromide). Suitable anionic agents are soaps; salts of aliphatic mono ester of sulphuric acid, for example sodium lauryl sulphate; and salts of sulphonated aromatic compounds, for example sodium dodecylbenzenesulphonate, sodium, calcium, and ammonium lignosulphonate, butylnaphthalene sulphonate, and a mixture of the sodium salts of diisopropyl and triisopropyl-naphthalenesulphonic acid. Suitable non-ionic agents are the condensation products of ethylene oxide with fatty alcohols such as oleyl alcohol and cetyl alcohol, or with alkylphenols such as octyl- or nonyl- phenol (e.g. Agral 90) or octylcresol. Other non-ionic agents are the partial esters derived from long chain fatty acids and hexitol arthydrides, for example sorbitan monolaurate; the condensation products of the partial ester with ethylene oxide; the lecithins; and silicone surface active agents (water soluble surface active agents having a skeleton which comprises a siloxane chain e.g. Silwet L77). A suitable mixture in mineral oil is Atplus 411F.

The aqueous solutions or dispersions may be prepared by dissolving the active ingredient in water or an organic solvent optionally containing wetting or dispersing agent(s) and then, when organic solvents are used, adding the mixture so obtained to water optionally containing wetting or dispersing agent(s). Suitable organic solvents include, for example, ethylene di-chloride, isopropyl alcohol, propylene glycol, diacetone alcohol, toluene, kerosene, methylnaphthalene, the xylenes and trichloroethylene.

The compositions for use in the form of aqueous solutions or dispersions are generally supplied in the form of a concentrate containing a high proportion of the active ingredient, and the concentrate is then diluted with water before use. The concentrates are usually required to withstand storage for prolonged periods and after such storage, to be capable of dilution with water to form aqueous preparations which remain homogeneous for a sufficient time to enable them to be applied by conventional spray equipment. Concentrates conveniently contain 20–90%, preferably 20–70%, by weight of the active ingredient(s). Dilute preparations ready for use may contain varying amounts of the active ingredient(s) depending upon the intended purpose; amounts of 0.01% to 10.0% and preferably 0.14 to 2%, by weight of active ingredient(s) are normally used.

A preferred form of concentrated composition comprises the active ingredient which has been finely divided and which has been dispersed in water in the presence of a surface-active agent and a suspending agent. Suitable suspending agents are hydrophilic colloids and include, for example, polyvinylpyrrolidone and sodium carboxymethylcellulose, and the vegetable gums, for example gum acacia and gum tragacanth. Preferred suspending agents are those which impart thixotropic properties to, and increase the viscosity of the concentrate. Examples of preferred suspending agents include hydrated colloidal mineral silicates, such as montmorillonite, beidellite, nontronite, hectorite, saponite, and saucorite. Bentonite is especially preferred. Other suspending agents include cellulose derivatives and polyvinyl alcohol.

The rate of application of the compounds of the invention will depend on a number of factors including, for example, the compound chosen for use, the identity of the plants whose growth is to be inhibited, the formulations selected for use and whether the compound is to be applied for foliage or root uptake. As a general guide, however, an application rate of from 0.001 to 20 kilograms per hectare is suitable while from 0.025 to 10 kilograms per hectare may be preferred.

The compositions of the invention may comprise, in addition to one or more compounds of the invention, one or more compounds not of the invention but which possess biological activity. Accordingly in yet a still further embodiment the invention provides a herbicidal composition comprising a mixture of at least one herbicidal compound of formula (I) as hereinbefore defined with at least one other herbicide.

The other herbicide may be any herbicide not having the formula (I). It will generally be a herbicide having a complementary action in the particular application.

Examples of useful complementary herbicides include:

A. benzo-2,1,3-thiadiazin-4-one-2,2-dioxides such as bentazone;

B. hormone herbicides, particularly the phenoxy alkanoic acids such as MCPA, MCPA-thioethyl, dichlorprop, 2,4,5-T, MCPB, 2,4-D, 2,4-DB, mecoprop, trichlopyr, clopyralid, and their derivatives (eg. salts, esters and amides);

C. 1,3 dimethylpyrazole derivatives such as pyrazoxyfen, pyrazolate and benzofenap;

D. Dinitrophenols and their derivatives (eg. acetates) such as dinoterb, dinoseb and its ester, dinoseb acetate;

E. dinitroaniline herbicides such as dinitramine, trifluralin, ethalflurolin, pendimethalin, oryzalin;

F. arylurea herbicides such as diuron, flumeturon, metoxuron, neburon, isoproturon, chlorotoluron, chloroxuron, linuron, monolinuron, chlorobromuron, daimuron, methabenzthiazuron;

G. phenylcarbamoyloxyphenylcarbamates such as phenmedipham and desmedipham;

H. 2-phenylpyridazin-3-ones such as chloridazon and norflurazon;

I. uracil herbicides such as lenacil, bromacil and terbacil;

J. triazine herbicides such as atrazine, simazine, aziprotryne, cyanazine, prometryn, dimethametryn, simetryne, and terbutryn;

K. phosphorothioate herbicides such as pipernphos, bensulide, and butamifos;

L. thiolcarbamate herbicides such as cycloate, vernolate, molinate, thiobencarb, butylate* , EPTC* , tri-allate, di-allate, esprocarb, tiocarbazil, pyridate, and dimepiperate;

M. 1,2,4-triazin-5-one herbicides such as metamitron and metribuzin;

N. benzoic acid herbicides such as 2,3,6-TBA, dicamba and chloramben;

O. anilide herbicides such as pretilachlor, butachlor, alachlor, propachlor, propanil, metazachlor, metolachlor, acetochlor, and dimethachlor;

P. dihalobenzonitrile herbicides such as dichlobenil, bromoxynil and ioxynil;

Q. haloalkanoic herbicides such as dalapon, TCA and salts thereof;

R. diphenylether herbicides such as lactofen, fluroglycofen or salts or ester thereof, nitrofen, bifenox, aciflurofen and salts and esters thereof, oxyfluorfen, fomesafen, chlornitrofen and chlomethoxyfen;

S. phenoxyphenoxypropionate herbicides such as diclofop and esters thereof such as the methyl ester, fluazifop and esters thereof, haloxyfop and esters thereof, quizalofop and esters thereof and fenoxaprop and esters thereof such as the ethyl ester;

T. cyclohexanedione herbicides such as alloxydim and salts thereof, sethoxydim, cycloxydim, tralkoxydim, and clethodim;

U. sulfonyl urea herbicides such as chlorosulfuron, sulfometuron, metsulfuron and esters thereof; benzsulfuron and esters thereof such as DPX-M6313, chlorimuron and esters such as the ethyl ester thereof pirimisulfuron and esters such as the methyl ester thereof, 2-[3-(4-methoxy-6-methyl-1,3,5-triazin-zyl)-3-methylureidosulphonyl] benzoic acid esters such as the methyl ester thereof (DPX-LS300) and pyrazosulfuron;

V. imidazolidinone herbicides such as imazaquin, imazamethabenz, imazapyr and isopropylammonium salts thereof, imazethapyr;

W. arylanilide herbicides such as flamprop and esters thereof, benzoylprop-ethyl, diflufenican;

X. amino acid herbicides such as glyphosate and glufosinate and their salts and esters, sulphosate and bialaphos;

Y. organoarsenical herbicides such as monosodium methanearsonate (MSMA);

Z. herbicidal amide derivative such as napropamide, propyzamide, carbetamide, tebutam, bromobutide, isoxaben, naproanilide and naptalam;

AA. miscellaneous herbicides including ethofumesate, cinmethylin, difenzoquat and salts thereof such as the methyl sulphate salt, clomazone, oxadiazon, bromofenoxim, barban, tridiphane, flurochloridone, quinchlorac, mefanacet, and triketone herbicides such as sulcotrione;

BB. Examples of useful contact herbicides include: bipyridylium herbicides such as those in which the active entity is paraquat and those in which the active entity is diquat;

* These compounds are preferably employed in combination with a safener such as dichlormid.

The invention is illustrated by the following Examples. (The preparation of intermediates is described in the Preparative Examples). The abbreviations used in the Examples have the following meanings:

NMR spectrum: nuclear magnetic resonance spectrum which were recorded at 270 or 400 MHz. (This refers to the proton magnetic resonance spectrum unless otherwise stated). The following abbreviations are used to indicate the multiplicity of the peaks in the NMR spectrum: s (singlet); d (doublet); t (triplet); q (quartet) quin (quintet) m (multiplet; br (broad).

IR spectrum: infra-red absorption spectrum.
MS: mass spectrum

GC: gas chromatography TLC: thin layer chromatography
m.p.: melting point b.p: boiling point

EXAMPLE 1

Preparation of 3-t-Butylcarbamoyloxy-1-(3-trifluoromethyl)phenyl-pyrrolidine-2-thione
(Compound No. 1)

3-t-Butylcarbamoyloxy-1-(3-trifluoromethyl)phenyl-2-pyrrolidinone (0.25 g) was dissolved in toluene (25 ml) and stirred under nitrogen at room temperature. To this solution was added diisopropylethylamine (0.479 g) and Lawesson's Reagent (2,4-bis(4-methoxyphenyl)-1,3-dithia-2,4-diphosphetane-2,4-disulphide) (1.47 g), and the reaction mixture heated to 80–90° C. for 80 minutes. The reaction mixture was then allowed to cool to room temperature and evaporated to dryness under reduced pressure. The residue was purified by silica gel chromatography (20–30% ethyl acetate-hexane as eluant) to give a solid which was further purified by recrystallisation from ethyl acetate-hexane. The title compound was obtained as a white solid, yield 0.169 g, m.p. 151.5°–152.5° C. $^1$H NMR (CDCl$_3$): δ1.36 (9H, s); 2.21 (1H, m); 2.79 (1H, m); 4.09 (2H, m); 4.92 (1H, broad s); 5.59 (1H, t); 7.59 (2H, m); 7.84 (2H, m). MS: m/e 360 (M$^+$).

Preparative Example 1.

Preparation of 3-hydroxy-1-(3-trifluoromethyl)phenyl-2-pyrrolidinone

Step 1 Preparation of 1-(3-trifluoromethyl)phenyl-2-pyrrolidinone-3-carboxylic acid A suspension of 6,6-dimethyl-5,7-dioxaspiro[2,5]octane-4,8-dione (prepared as described in Organic Syntheses, Volume 60, p66–68) (8.00 g) in 3-trifluoromethylaniline (8.05 g) was stirred at room temperature for 24 hours. The mixture was filtered, and the insoluble solid was washed with chloroform. The combined filtrates were washed with 2M hydrochloric acid, brine and then dried (MgSO$_4$). Evaporation of the solvent under reduced pressure left a brown solid, which was recrystallised from chloroform/hexane to give the product as a white, crystalline solid, yield 4.10 g, mp 135°–136° C. (dec).

$^1$H nmr (CDCl$_3$): δ2.47–2.67 (2H, m), 3.70 (1H, t), 3.92–4.01 (2H, m), 7.00 (broad), 7.45–7.60 (2H, m), 7.81–7.90 (2H, m)

Step 2 Preparation of 1-(3-trifluoromethyl)phenyl-2-pyrrolidinone 1-(3-trifluoromethyl)phenyl-2-pyrrolidinone-3-carboxylic acid (prepared as in Step 1 above) (3.60 g) was heated to its melting point, and heating was continued until effervescence ceased (ca 50 minutes). The melt was cooled, dissolved in diethyl ether, and treated with decolourising charcoal. The charcoal was filtered off, and the solvent was removed under reduced pressure to leave a solid residue. This was recrystallised from hexane to give the product as colourless needles, yield 2.209, mp 67°–68° C.

$^1$H nmr (CDCl$_3$): 67.19 (2H, quin), 2.62 (2H, t), 3.89 (2H, t), 7.35–7.53 (2H, m), 7.81–7.93 (2H, m)

MS: m/e 229 (M$^+$)

Step 3 Preparation of 3-hydroxy-1-(3-trifluoromethyl)phenyl-2-pyrrolidinone

A stirred solution of 1-(3-trifluoromethyl)phenyl-2-pyrrolidinone (prepared as in Step 2 above) (1.10 g) in dry tetrahydrofuran (5 ml) was cooled to −70° C. under a nitrogen atmosphere, and a solution of lithium hexamethyldisilazide in hexanes (1.0M, 4.9 ml) was added dropwise. The resultant pale yellow suspension was then treated with a solution of N-toluenesulphonyl-3-phenyloxaziridine (prepared as described in Journal of Organic Chemistry, 1988, 53, 2087) (2.00 g) in dry tetrahydrofuran (5 ml). The resultant pale yellow solution was allowed to warm to room temperature, and was then quenched with water and acidified to pH5 using 2M hydrochloric acid. The mixture was extracted with diethyl ether (×2), and the combined extracts were washed with water, dried (MgSO$_4$) and evaporated under reduced pressure to leave an oil. Purification by silica gel chromatography, eluting with ethyl acetate/hexane mixtures, afforded the title compound as a clear gum, yield 0.26 g.

$^1$H nmr (CDCl$_3$): δ1.62 (1H, broad s), 2.12 (1H, m), 2.63 (1H, m), 3.72–3.90 (2H, m), 4.51 (1H, m), 7.39–7.58 (2H, m), 7.77–8.02 (2H, m)

MS: m/e 245 (M$^+$)

Step 4 3-t-butylcarbamoyloxy-1-(3-trifluoromethyl)phenyl-2-pyrrolidinone

A stirred solution of 3-hydroxy-1-(3-trifluoromethyl)phenyl-2-pyrrolidinone (prepared as in Step 3 above) (0.220 g) in dichloromethane (2 ml) was treated with tert-butyl isocyanate (0.063 g) followed by triethylamine (0.084 ml). The solution was stirred for 24 hours, then evaporated under reduced pressure. Purification of the residue by silica gel chromatography, eluting with ethyl acetate/hexane mixtures, afforded the title compound as a clear gum, yield 0.060 g.

$^1$H nmr (CDCl$_3$): δ1.35 (9H, s), 2.13 (1H, m), 2.73 (1H, m), 3.80–3.89 (2H, m), 4.94 (1H, broad s), 5.38 (1H, t), 7.38–7.53 (2H, m), 7.89–7.95 (2H, m)

Biological Data

The herbicidal activity of the compounds was tested as follows: Each chemical was formulated in one of two ways. Either the chemical was dissolved in an appropriate amount of water, dependent on the amount of solvent/surfactant blend required such that the total volume is 5 cm$^3$. Then a solvent sufficient blend comprised 78.2 gm/liter of Tween 20 and 21.8 gm/liter of Span 80 adjusted to 1 liter using methylcyclohexanone was added to the solution. Alternatively, the chemical was dissolved in water to the required concentration and 0.1% Tween added. Tween 20 is a Trade Mark for a surface-active agent comprising a condensate of 20 molar proportions of ethylene oxide with sorbitan laurate. Span 80 is a Trade Mark for a surface-active agent comprising sorbitan mono-laurate. If the chemical did not dissolve, the volume was made up to 5 cm$^3$ with water, glass beads were added and this mixture was then shaken to effect dissolution or suspension of the chemical, after which the beads were removed. In all cases, the mixture was then diluted to the required spray volume. If sprayed independently, volumes of 25 cm$^3$ and 30 cm$^3$ were required for post-emergence tests; if sprayed together, 45 cm$^3$ was required. The sprayed aqueous emulsion contained 4% of the initial solvent/surfactant mix and the test chemical at an appropriate concentration.

The spray compositions so prepared were sprayed on to young pot plants (post-emergence test) at a spray volume equivalent to 1000 liters per hectare. Damage to plants was assessed 13 days after spraying by comparison with untreated plants, on a scale of 0 to 9 where 0 is 0% damage, 1 is 1–5% damage, 2 is 6–15% damage, 3 is 16–25% damage, 4 is 26–35% damage, 5 is 36–59% damage, 6 is 60–69% damage, 7 is 70–79% damage, 8 is 80–89% damage and 9 is 90–100% damage.

In a test carried out to detect pre-emergence herbicidal activity, crop seeds were sown at 2 cm depth and weed seeds at 1 cm depth beneath compost and sprayed with the compositions at the rate of 1000 liters per hectare. 20 days after spraying, the seedlings in the sprayed plastic trays were compared with the seedlings in unsprayed control trays, the damage being assessed on the same scale of 0 to 9.

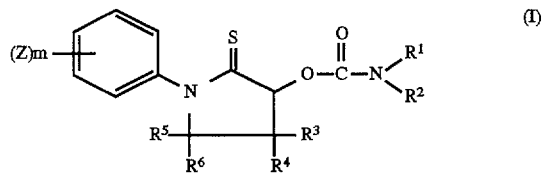

(I)

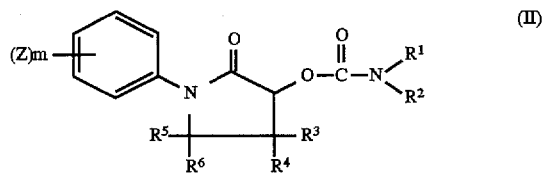

(II)

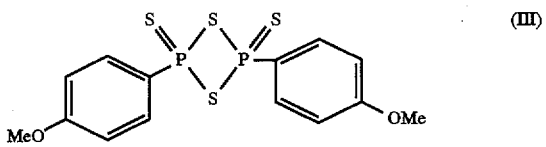

(III)

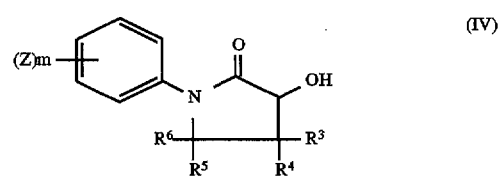

(IV)

(V)

(VI)

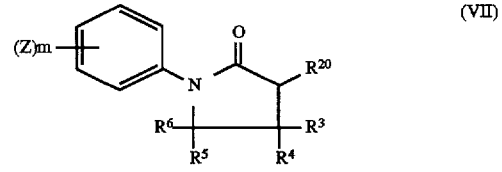

(VII)

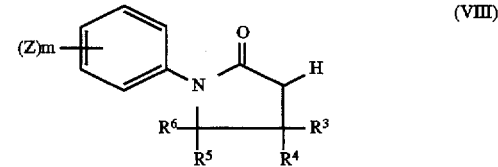

(VIII)

(XI)

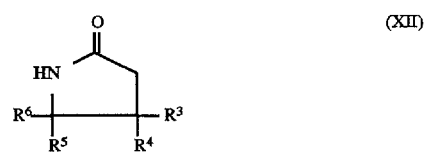

(XII)

11
-continued

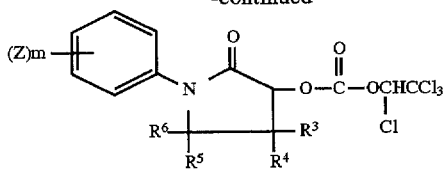 (XIII)

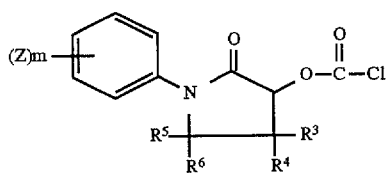 (XIV)

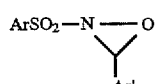 (XVII)

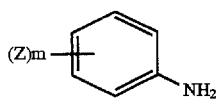 (XVIV)

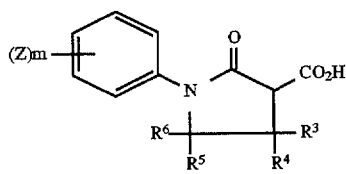 (XX)

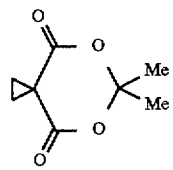 (XXI)

We claim:
1. A compound of formula (I):

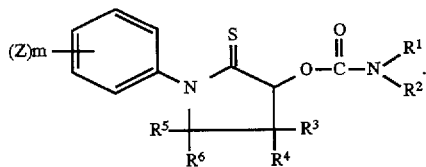 (I)

Wherein $R^1$ and $R^2$ are each independently hydrogen, optionally substituted lower hydrocarbyl, or optionally substituted heteroaryl, or $R^1$ and $R^2$ together with the nitrogen atom to which they are attached, form a heterocyclic ring; $R^3$, $R^4$, $R^5$ and $R^6$ are independently H or $C_{1-4}$ alkyl; Z represents halogen, optionally substituted lower hydrocarbyl, optionally substituted lower hydrocarbyloxy, optionally substituted lower hydrocarbylthio, hydrocarbylsulphinyl, or hydrocarbylsulphonyl, cyano,

12 nitro, CHO, NHOH, $ONR^7R^{7'}$, $SF_5$, CO(optionally substituted lower hydrocarbyl), acylamino, $COOR^7$, $SO_2NR^8R^9$, $CONR^{10}R^{11}$, $OR^{12}$ or $NR^{13}R^{14}$ where $R^7$, $R^{7'}$, $R^{7''}$, $R^8$, $R^9$, $R^{10}$ and $R^{11}$ are independently H or lower hydrocarbyl; $R^{12}$ is hydrogen, $SO_2$ lower hydrocarbyl or $COR^{15}$; $R^{13}$ and $R^{14}$ are independently lower hydrocarbyl, lower hydrocarbyloxy or a group $R^{12}$; $R^{15}$ is $OR^{16}$, $NR^{17}R^{18}$, hydrogen or lower hydrocarbyl; $R^{16}$ is lower hydrocarbyl, $R^{17}$ and $R^{18}$ are independently hydrogen or lower hydrocarbyl provided that when there are two or more substituents Z, they may be the same or different; and m is 0 or an integer from 1 to 5.

2. A process of severely damaging or killing unwanted plants, which comprises applying to the plants, or to the growth medium of the plants, a herbicidally effective amount of a compound of formula (I) as defined in claim 1.

3. A herbicidal composition comprising a compound of formula (I) as defined in claim 1 in combination with a herbicidal carrier or diluent.

4. A compound of formula (I) as defined in claim 1, wherein Z represents methyl, ethyl, n-propyl, iso-propyl, trifluoromethyl, difluoromethyl, pentafluoroethyl, trichloromethyl, ethoxyvinyl, fluorine, chlorine, bromine, iodine, methoxy, ethoxy, n-propoxy, iso-propoxy, trifluoromethoxy, tetrafluoroethoxy, cyano, nitro, amino, mono- or dialkylamino in which each alkyl group may have from 1 to 6 carbon atoms, hydroxylamino, acyl, methylthio, methylsulphinyl, methylsulphonyl, trifluoromethylthio, trifluoromethylsulphinyl, trifluoromethylsulphonyl, sulphonamido, carboxy, alkoxycarbonyl in which the alkoxy group may have from 1 to 6 carbon atoms, carboxyamide in which the groups attached to the N atom may be hydrogen or optionally substituted lower hydrocarbyl or acylamino; provided that when there are two or more substituents Z, they may be the same or different.

5. A compound of formula (I) as defined in claim 4, wherein Z represents $CF_3$, $OCF_3$, $OCHF_2$, $CHF_2$, OMe, F, Cl, Br, I, $NH_2$, $NO_2$, CN, $C_{1-4}$alkyl, $C_{1-4}$alkoxy, $COC_{1-4}$alkyl, $NHCOC_{1-4}$ alkyl, $SO_2C_{1-4}$alkyl, $OCF_2CHF_2$, $CF_2CF_3$, $OCF_2CHF_2$ or $SO_2NR^8R^9$, provided that when there are two or more substituents Z, they may be the same or different.

6. A compound of formula (I) as defined in claim 1, wherein m represents 1, 2 or 3.

7. A compound of formula (I) as defined in claim 1, wherein $R^1$ represents iso-propyl, sec-butyl, t-butyl, $C(CH_3)_2C\equiv CH$, $C(CH_3)_2CH\equiv CH_2$, $C(CH_3)_2CH_2CH_3$ or a 3–6 membered cycloalkyl ring, optionally substituted by $CH_3$ or $C\equiv CH$ at the α position of the cycloalkyl ring.

8. A compound of formula (I) as defined in claim 1, wherein $R^2$ is hydrogen or $C_{1-4}$ alkyl.

9. A compound of formula (I) as defined in claim 1, wherein $R^3$, $R^4$, $R^5$ and $R^6$ are hydrogen.

* * * * *